United States Patent [19]

Caranci

[11] Patent Number: 5,002,214
[45] Date of Patent: Mar. 26, 1991

[54] MEDICAL SPRAY CONTAINER CARRYING CASE

[76] Inventor: Mark W. Caranci, 2180 SE. 7th St., Pampano Beach, Fla. 33062

[21] Appl. No.: 456,508

[22] Filed: Dec. 26, 1989

[51] Int. Cl.$^5$ .................................................. A45F 5/02
[52] U.S. Cl. .................................. 224/252; 224/228; 224/240; 224/904
[58] Field of Search ............ 224/252, 253, 240, 239, 224/235, 236, 904, 269, 224, 228; 128/200.23, 203.15; 604/58

[56] References Cited

U.S. PATENT DOCUMENTS

| | | | |
|---|---|---|---|
| 1,287,330 | 12/1918 | Jennings | 224/228 |
| 1,338,794 | 5/1920 | Spalding | 224/228 |
| 1,375,442 | 4/1921 | Batchelder | 224/228 |
| 1,610,344 | 12/1926 | Williams | 224/252 X |
| 1,648,565 | 11/1927 | Primley | 224/240 X |
| 2,315,095 | 3/1943 | Rhodes | 224/228 X |
| 2,813,669 | 11/1957 | Frieder et al. | 224/236 X |
| 3,297,217 | 1/1967 | Nichols | 224/240 |
| 3,445,046 | 5/1969 | Wilson | 224/253 X |
| 4,214,686 | 7/1980 | Dostourian | 224/252 |
| 4,479,596 | 10/1984 | Swanson | 224/236 |
| 4,588,116 | 5/1986 | Litman | 224/253 |
| 4,705,086 | 11/1987 | O'Neill | 224/252 X |
| 4,838,466 | 6/1989 | Holmstrom | 224/253 X |

FOREIGN PATENT DOCUMENTS 0106614  5/1918  United Kingdom ................ 224/239

*Primary Examiner*—Henry J. Recla
*Assistant Examiner*—Casey Jacyna
*Attorney, Agent, or Firm*—Harry W. Barron

[57] ABSTRACT

A case holds a medical spray container system, including the plastic container and a cylinder of medical fluid which is atomized and dispensed through an opening normally covered by a cap when not in use. The case is fabricated from three strips of woven material affixed together to hold the container and to protect the cap from falling off. Two of the three pieces of material are formed in closed loop configurations to fit respectively over the base and top of the container, including the attached cap. The third piece of material interconnects the first two pieces and functions as a hinge and cap cover to prevent the container cap from becoming dislodged and lost or damaged. The third piece is secured within the closed loop formed over the cap and top at a position adjacent to the cap. An elastic strip is also provided to permit the cylinder of spray to be replaced without the necessity of removing the entire container.

7 Claims, 2 Drawing Sheets

MEDICAL SPRAY CONTAINER CARRYING CASE

This invention relates to a spray container case, and more particularly, to such a case, attachable to belt, waistband, purse or the like, for holding a nasal or oral spray and for easily being opened when it is necessary to use the spray.

BACKGROUND OF THE INVENTION

People with asthma and other pulmonary ailments must use nasal and oral sprays in order to lead normal lives. Typically, these sprays are contained in metal cylinders and an atomized liquid spray is provided by depressing a nozzle extending from the cylinder. Plastic containers are typically provided by the manufacturer of the spray to receive and hold the nozzle of the spray cylinder and emit the spray through an opening in the container when pressure is provided against the bottom of the spray cylinder. Such containers are necessary to the practical and easy use of the medical spray.

One of the problems with the modern medical spray systems described above is that the spray cylinder and container are not easily carried by a user. For a person with a sever pulmonary ailment, the need for using the spray occurs almost instantaneously and without warning or predictability. However, before the spray can be used, it must be found. For a person that is bed ridden, or a person who sits at a desk all day long, it is an easy task to keep the spray system at the same place all of the time. For example, the spray may be placed on a night stand adjacent to the bed, or in a particular drawer of a desk.

For a person who is not located at the same place all day long, the spray system must be carried with the person and must be easily and quickly retrievable. For women, the spray can be carried in a purse, although it may be difficult to quickly find if merely thrown in the purse. For men, carrying the spray is a particular problem because of its large size. For example, the spray cylinder and plastic container furnished by the manufacturer is typically too big to fit into an average pants pocket, and even if it does fit, it is uncomfortable and doesn't look good.

The plastic spray containers furnished by the manufacturers of the sprays all contain a cap which protects the opening of the container while it is not being used. The purpose of this cap is to prevent dirt and bacteria from building up around the spray opening and is an important component part of the existing spray systems. The caps are typically plastic component parts which are press fit into place, and which may be removed with a slight force by the user. However, the press lock system often fails after prolonged use and the cap fall off and becomes lost. Further, carrying the spray container in a purse or pants pocket will invariably cause the cap to become dislodged. In this instance, the entire spray container could be rendered useless if sufficient dirt and bacteria enter the spray opening. At a minimum, the plastic container must be replaced, thereby causing a needless trip to the pharmacy to purchase a new one.

In addition, the spray cylinder is held in the plastic container by press fitting the cylinder nozzle into a nozzle receptacle. If the connection between the nozzle and nozzle receptacle becomes lose, the cylinder can fall out and become lost or damaged. For a person dependent upon the medical spray, this may be a disastrous result. Further, many medical sprays are very expensive and the loss of a container results in the needless waste of a lot of money for the user.

What is needed is a container for the spray system which can be easily affixed to a belt, waistband, purse or other object within the easy and quick reach of the user. Further, such container must be easy to use quickly and must further be designed to easily be opened, yet maintain the cap from being lost when closed.

DESCRIPTION OF THE PRIOR ART

In the past, many different cases for many different objects have been designed to fit on a belt, waistband, purse or other object. For example, reference is made to the following United States Patents as examples of devices affixable to an object, such as a person's belt, for holding a variety of different products:

U.S. Pat. No. 1,282,695 in the name of V. H. Jennings, entitled "Pocketed Carrier";

U.S. Pat. No. 1,895,074 in the name of E. R. Hagerstrom, entitled "Article Holster";

U.S. Pat. No. 2,700,492 in the name of H. Baetzing, entitled "Writing Instrument Holder";

U.S. Pat. No. 3,297,217 in the name of D. A. Nichols, entitled "Pipe Holder";

U.S. Pat. No. 4,399,934 in the name of C. L. Dupont, entitled "Belt Attached Carrier";

U.S. Pat. No. 4,479,596 in the name of A. W. Swanson, entitled "Carrying Case For Portable Electronic Paging Devices"; and U.S. Pat. No. 4,775,083 in the name of M. S. Berger et al, entitled "Portable Radio Carrying Case".

None of the carrying cases described in each of these aforementioned patents is useful to contain the medical spray system described above, and particularly for containing and preventing the loss of the cap over the spray opening.

SUMMARY OF THE INVENTION

In accordance with one aspect of this invention, there is provided a case for a medical spray system comprising a first piece of material affixed in a closed loop to form at least two sides and a second piece of material having one end thereof affixed to one side of the first piece of material, the second piece of material extending upward from the first piece of material. The case system further includes a third piece of material affixed to the second piece of material at one position thereof which extends around the second piece of material at a second portion thereof. Finally, the case system includes means for affixing the other end of the second piece of material to the other side of the first piece of material.

BRIEF DESCRIPTION OF THE DRAWINGS

One preferred embodiment of the subject invention is hereafter described with reference to the following Figures, in which.

DETAILED DESCRIPTION

Figure 1:
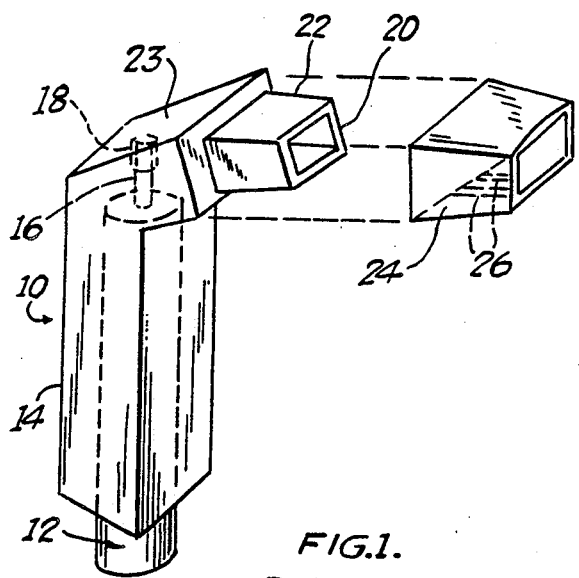
FIG. 1 is a perspective view of the prior art plastic spray container system including a cylinder of medical spray affixed therein.

Referring to FIG. 1, a typical prior art plastic spray container case 10 is shown holding a typical prior art cylinder 12 containing medication in the base 14 thereof. Cylinder 12 includes a nozzle 16 extending upward therefrom which, when depressed, allows a atomized version of the medication to be emitted. Container 10 is sized to permit cylinder 12 to fit within base 14 and includes a nozzle receiver 18 adapted to receive and hold nozzle 16 and to redirect the atomized medication, or spray, by approximately eighty degrees. Container 10 further includes an exit opening 20 and an exit shoulder 22 extending from the top 23 of container 10. Both shoulder 22 and opening 20 are aligned at approximately eighty degrees relative to the alignment of cylinder 12 and through which the spray passes when cylinder 12 is depressed towards nozzle receiver 18.

A container cap 24 is also provided as a part of container system 10 and is adapted to fit over shoulder 22 in order to protect opening 20 from dirt and bacteria when spray system is not being used. Cap 24 may include a plurality of ribs 26 on the inside surface thereof for maintaining cap 24 on shoulder 22 when forced thereagainst by a user. However, ribs 26 must be designed to permit the easy removal of cap 24 whenever the user of spray container 10 desires to use the spray for medical purposes. Thus, cap 24 cannot be held too tightly, or the designed use of the spray system 10 will be inhibited. This requirement results in the cap eventually becoming loose and falling off of spray container 10 after ribs 26 become worn, or cap 24 becomes slightly bent out of its original shape. Further, jostling within a purse or pocket could dislodge cap 24 from shoulder 22. If this happens, dirt and bacteria will build up inside container 10 around nozzle receiver 18. This dirt and bacteria could cause the medical spray in cylinder 12 to become contaminated and therefore not usable.

Figure 2:
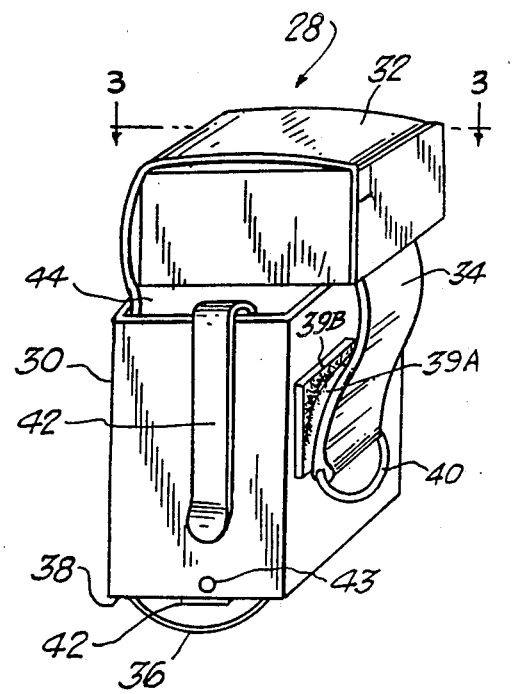
FIG. 2 is a perspective view of the medical spray container carrying case of the subject invention for holding the container and cylinder shown in FIG. 1.

Referring to FIG. 2, the basic carrying case 28 of the subject invention will now be described. Carrying case 28 includes a base 30, a cap 32 and a fastening strap 34, each of which is fabricated of a heavy woven material available in long strips. As will be described hereafter, three pieces, cut from the strips, are used to fabricate and interconnect the base 30, cap 32 and fastening strap 34.

In addition to the base 30, cap 32 and fastening strap 34, case 28 includes an elastic strap 36 connected from one to the other side of the bottom 38 of base 30. Elastic strap is designed to hold the bottom of cylinder 12 (seen in FIG. 1) so that the nozzle 16 cannot become free of the nozzle holder 18. By making strap 36 out of an elastic, or stretchable, material, it is an easy matter to move, partially by stretching, the strap 36 to one side in order to change cylinder 12 when it becomes empty.

Further, case 28 includes one type 39A of a hook and loop material affixed to the side of fastening strap 34 facing base 30 and the other type 39B of the hook and loop material affixed to the base 30 and positioned to be in alignment with the one portion 39A when strap 34 is fully extended downward away from cap 32. The presence of the hook and loop material permits the easy affixation of fastening strap 34 against base 30 and permits the easy release thereof when the user desires to utilize the medical spray. A handle 40 is affixed to the end of fastening strap 34 to further permit the quick release of the fastening strap 34 from base 30 and to permit the removal of cap 32 from around the cap 24 and top 22 of the inserted container 10.

Lastly, case 28 includes a clip 42 made of stainless steel, or other high tension spring material, held in place by a rivet 43, or other fastening means. Clip 42 is held by base 30 and permits case 28 to be easily fastened to the belt or waistband of the user, or to a purse or other item normally carried by the user. Further, the clip may be used to fasten the case 28 to any adaptable item where the user will always know the location of case 28. Alternatively, the clip 42 may be replaced with a hook and loop type fastening device.

Base 30 is sized to receive base 14 of spray container 10, which may be inserted therein through the top opening 44 of base 30. Cap 32 is sized and spaced from base 30 so as to fit over the top 23 and cap 24 covered shoulder 22 of container 10. Fastening strap 34 extends downward from the front of top 44 of case 28 and when lifted using handle 40 rotates top 44 away from the top of container 10 to expose cap 24. Thereafter, the user may remove cap 24 and use the spray system 10 in the normal manner. After using the spray, the user replaces cap 24 over shoulder 22 and pulls handle 40 downward. This causes cap 32 to cover the top 23 and cap 24 and prevent the loss of cap 24.

Figure 3:
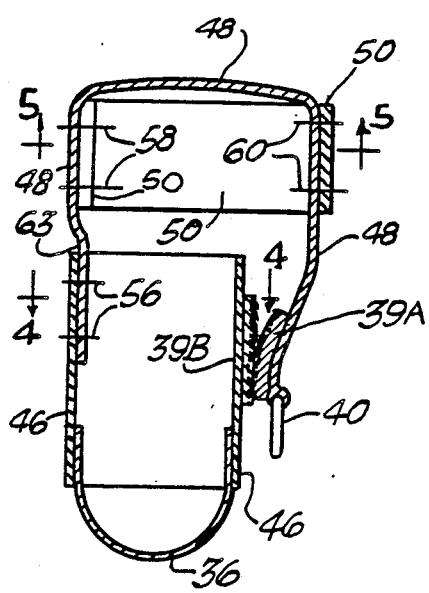
FIG. 3 is a cross-sectional view, taken across lines 3—3 of FIG. 2, showing a side view of the construction of the carrying case of the subject invention.
Figure 4:
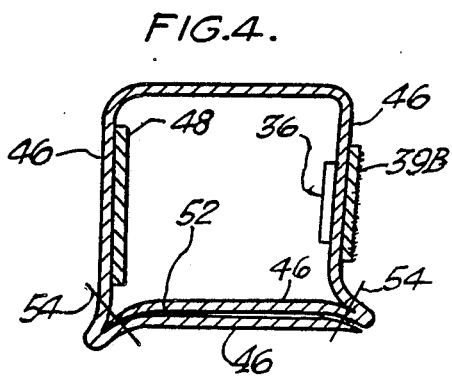
FIG. 4 is a cross-sectional view, taken across lines 4—4 of FIG. 3, showing a top view of the construction of the barrel of carrying case of the subject invention.
Figure 5:
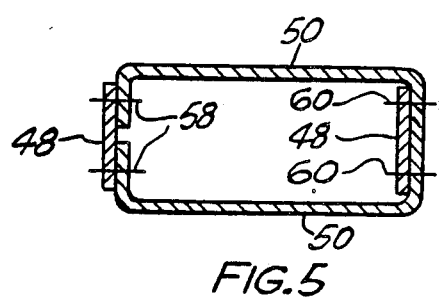
FIG. 5 is a cross-sectional view, taken across lines 5—5 of FIG. 3, showing a top view of the construction of the cap of carrying case of the subject invention.

Referring now to FIGS. 3 through 5, the manner of fabricating case 28 will now be described. As previously mentioned, there are three pieces of woven strip material 48, 50 and 52 utilized to construct the basic case 28. The first piece, or base strip, 46 of the woven strip material may be two inches wide and is used to form base 30. Base strip 46 is selected to be of a length so that when it is formed in a closed loop with the two ends overlapping to form an opening 52 sized to receive the back element of clip 42, as best seen in FIG. 4. Piece 48 may be sewn (or ultrasonically welded if appropriate materials, such as Nylon are used) at stitches 54 and the lengthwise edges of strip 46 may be bonded to prevent unraveling. If the material of strips 46, 48 and 50 is Nylon or other similar material, the lengthwise edge bonding may be accomplished by applying heat to the end to melt the stands of material together.

The second piece of woven strip material, or fastener strip, 48 is a one inch wide strip which has one end secured, such as by sewing or ultrasonic welding, to the interior of the back side of base strip 46, as best seen in FIG. 3. For example, fastening strip 48 may be secured to back strip 46 by threads 56. Fastening strip 48 is sized to be of sufficient length to fit entirely over top 22 and affixed cap 24 and thereafter extend down slightly past hook or loop material 39B. The other end of fastener strip 48 is secured back over itself in order to provide an opening for containing handle 40. When Handle 40 is inserted, the bottom of handle 40 should be near the bottom 38 of case 28.

The third piece of woven strip material, or cap strip, 50 is again a one inch wide strip and has both ends thereof affixed closely adjacent to one another against fastener strip 48. The center portion of strip 50 is also affixed to strip 48 so as to form a closed loop of strip 50, which is covered by strip 48, as best seen in FIGS. 3 and 5. Strips 48 and 50 are arranged so that strip 48 is on the sewn by stitches 58 on the outside of the formed closed loop at the back side of the formed cap cover, that is the side away from the position of cap 24. Further, strips 48 and 50 are arranged so that strip 48 is sewn by stitches 60 within the formed closed loop of strip 50 at the side of the closed loop adjacent to cap 24. In this manner, the facing edges of strip 50 are hidden by strip 48 at the rear of the closed loop and, in addition, when handle 40 is pulled upward, the minimum stress is placed upon the stitches 60 when the formed cap 32 is lifted off the cap 24 and top 22 of container 10. If strip 48 were placed on the outside of the closed loop formed by strip 50 at the position of stitches 60, then as handle 40 is lifted upward, the stitches 60 would be pulled apart.

The fastener strip 48, in the area 63 between the strips 46 and 50, acts as a hinge connection between base 30 and cap 32, formed by the closed loop of strip 50 with a top formed by strip 48. The hinge effect is particularly effective because of the double thickness material both above and below the hinge area 63 due to the fastening together of different ones of the strips 46, 48 and 50.

Figure 6:
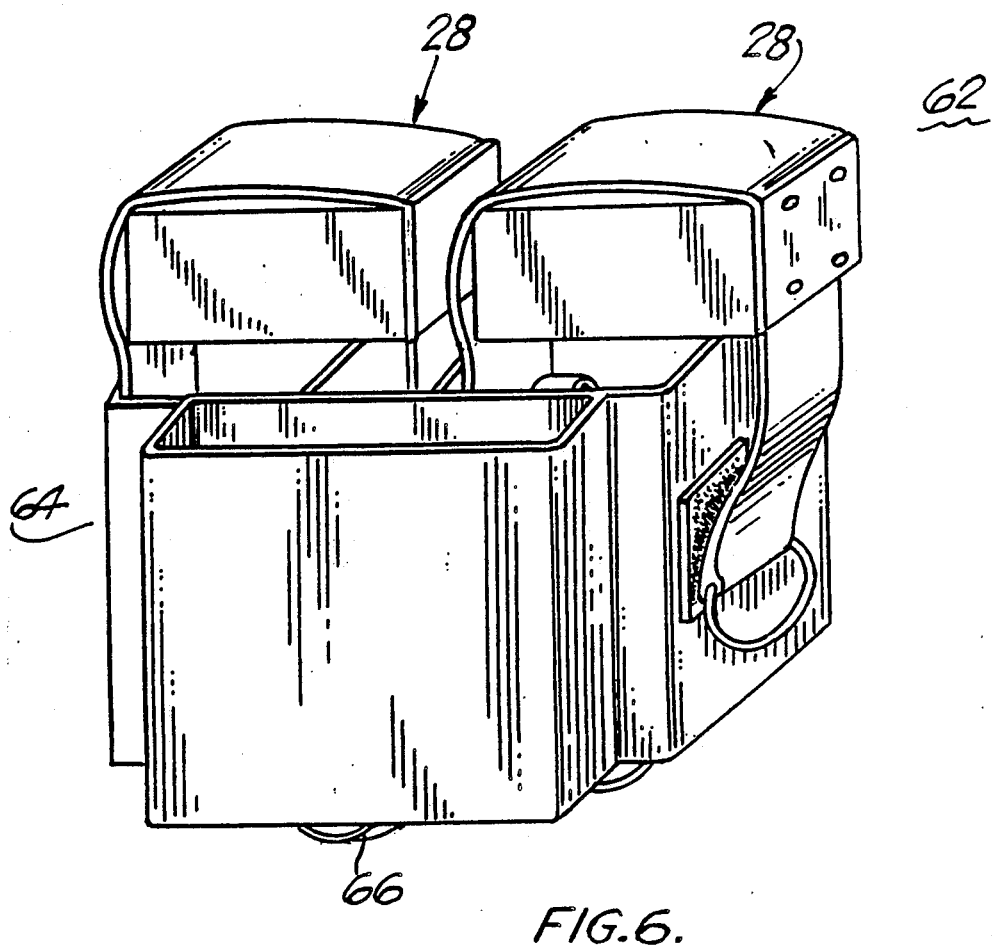
FIG. 6 is a second preferred embodiment of a medical spray container carrying case for containing two spray container systems and a pill box.

Referring now to FIG. 6, a case 62 for carrying two spray container systems 10, as well as a container for pills, is shown. Case 10 includes two cases 28 having the back ends thereof secured together. Further, the one side of the two cases 28 has a two inch strip of material 64 secured thereto to form a pocket for containing a pill box (not shown) for holding tabletized medication for the user. An elastic strap 66, similar to strap 36 may be affixed between material 64 and the two secured cases 28 to prevent the pill box from falling through the pocket formed by securing strip 64. Other designs using the basic design of the case 28 are also possible.

It should be noted that there are several different variations of the plastic container 10 available from different manufacturers of medical sprays. Because of the various different size and shape of containers 10 available on the market, or to be hereafter designed, it may be necessary to provide several different sized or shaped cases 28, although each case should be able to accept several closely sized containers 10.

What is claimed is:

1. A case for medical spray container having a barrel and a capped nozzle extending upward and outward from said barrel, said nozzle having a top and sides, said case comprising:

a first piece of material affixed in a closed loop, said first piece of material being sized to receive said barrel within said closed loop;

a second piece of material having one end thereof affixed to one side of said first piece of material, said second piece of material extending upward from said first piece of material;

a third piece of material having two ends, each affixed to said second piece of material at a first portion thereof, spaced from said one end of said second piece to form a closed loop, said third piece of material being and affixed to said second piece of material at a second portion thereof opposite said two ends, said third piece of material being sized to surround said sides of said capped nozzle, said second portion being spaced from said first portion by a distance selected to permit said third piece of material to cover said top of said capped nozzle, said second piece of material having an opposite end extending from said second portion of said third piece of material, and means for affixing said other end of said second piece of material to said first piece of material opposite said one side.

2. The invention according to claim 1 wherein said first piece of material has two open ends and wherein a fourth piece of material is affixed across one of said open ends, said one end being remote from said second piece of material, said fourth piece of material being sized and affixed to permit access to space within said closed loop.

3. The invention according to claim 2 wherein said other end of said second piece of material includes handle means for lifting said second piece of material.

4. The invention according to claim 3 wherein said case further includes a clip and said first piece of material is overlapped in forming said closed loop to form a receptacle for holding said clip.

5. The invention according to claim 1 wherein said other end of said second piece of material includes handle means for lifting said second piece of material.

6. The invention according to claim 1 wherein said case further includes a clip and said first piece of material is overlapped in forming said closed loop to form a receptacle for holding said clip.

7. The invention according to claim 1 wherein said means for affixing includes hook and loop fastener means.

* * * * *